(12) United States Patent
Guram et al.

(10) Patent No.: US 6,974,878 B2
(45) Date of Patent: Dec. 13, 2005

(54) CATALYST LIGANDS, CATALYTIC METAL COMPLEXES AND PROCESSES USING SAME

(75) Inventors: Anil Guram, Cupertino, CA (US); Cheryl Lund, Milpitas, CA (US); Howard W. Turner, Campbell, CA (US); Tetsuo Uno, San Francisco, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 479 days.

(21) Appl. No.: 09/956,157

(22) Filed: Sep. 18, 2001

(65) Prior Publication Data

US 2002/0137934 A1 Sep. 26, 2002

Related U.S. Application Data

(62) Division of application No. 09/814,393, filed on Mar. 21, 2001, now Pat. No. 6,316,663.

(51) Int. Cl.$^7$ ................................................ C07F 9/00
(52) U.S. Cl. ........................... 556/32; 556/33; 556/34; 556/42
(58) Field of Search ............................. 556/32, 33, 34, 556/42

(56) References Cited

U.S. PATENT DOCUMENTS

| | | | |
|---|---|---|---|
| 4,981,865 A | 1/1991 | Belliotti et al. | ............. 514/480 |
| 5,143,929 A | 9/1992 | Belliotti et al. | ............. 514/364 |
| 5,883,204 A | 3/1999 | Spencer et al. | |
| 5,919,983 A | 7/1999 | Rosen et al. | |

FOREIGN PATENT DOCUMENTS

| | | | | |
|---|---|---|---|---|
| DE | 29 00 260 | | 7/1979 | ........... C07C/95/08 |
| EP | 0 889 061 A1 | | 1/1999 | |
| EP | 0 953 571 A1 | | 11/1999 | |
| WO | WO 97/27179 | | 7/1997 | ......... C07D/219/12 |
| WO | WO 98/17650 | | 4/1998 | ......... C07D/219/04 |
| WO | WO 98/30609 | | 7/1998 | ........... C08F/10/00 |
| WO | WO 99/05154 | | 2/1999 | ........... C07F/19/00 |
| WO | WO 99/54337 | | 10/1999 | ............. C07F/9/50 |

OTHER PUBLICATIONS

Allan, J.R. et al, Thermochimica Acta (1994) 231 (1–2) 121–8.*
Bassi, P.S., Journal of Thermal Analysis (1997), 49(3) 1153–1160.*
OSA, T et al Chemical and Pharmaceutical Bulletin (1986) 34 (5) 881–7.*
Rice, C.A. et al Inorganica Chimica Acta (1982) 59 (1) 33–9.*
Allen, J.R. et al, Thermochimica Acta (1994) 231(1–2) 121–8.*
Bassi, P.S., Journal of Thermal Analysis (1997), 49(3) 1153–1160.*
Osa, T et al. Chemical and Pharmaceutical Bulletin (1986), 34(5) 881–7.*
Rice, C.A. et al Inorganica Chimica Acta (1982) 59(1) 33–9.*
Baum et al., "Nickel–Catalyzed Transformations of 2,1–Benzisoxazoles With Organozinc Reagents," *J. Organic Chem.* 52, (1987) pp. 2983–2988.
Black et al., "Metal Template Reactions," *Aust. J. Chem.* 23 (1970) pp. 2055–2065.
Chemical Abstracts, 70(15) Apr. 14, 1969, Columbus, Ohio, US, Abstract No. 67938a, A. Sallmann et al., "Analgesic cinnamic acid derivatives" p. 331.
Chemical Abstracts, 98(15) Apr. 11, 1983, Columbus, Ohio, US, Abstract No. 125625n, Nissan Chemical Industries: "Anthranilaldehyde Derivatives" p. 596.
Coyne et al., "3,4–Dihydro–2(1H)–quinazolinones," *J. Med. Chem.*, 11, 541 (1968) pp. 1208–1213.
Dabrowski, et al., "Symmetrically Bifurcate Hydrogen Bonding–III., " *Tetrahedron*, 29, (1973) pp. 2257–2260.
Fischer, "Lichtreaktionen von N–Aryl–oxindolen mit nucleophilen Agienten", *Chem, Ber.* 102, (1969) pp. 3495–3499.
Ishii et al., "Fischer Indolization and Its Related Compounds. XXIII. Fischer Indolization of Ethyl Pyruvate 2–(2, 6–Dimethoxyphenyl)phenylhydrazone," *Chem. Pharm. Bull.* 38(8) (1990) pp. 2118–2126.
Lehmann et al., "Zur reduzierenden Spaltung von Chinazolin–2,4–dionen," *Arch. Pharm. (Weinheim)* 315, (1982) pp. 967–969.
Okawa et al., "Macro Chelate Rings. III., "*Bulletin of the Chemical Society of Japan*, 43, No. 6, (1970) pp. 1729–1733.
Rosevear et al., "The Preparation of Some 2–Nitroacridines and Related Compounds," *Aust. J. Chem.* 34, (1981), pp. 839–853.

* cited by examiner

Primary Examiner—Paul J. Killos

(57) ABSTRACT

A new ligands that include a benzene ring in the backbone can be combined with a metal or metal precursor compound or formed into a metal-ligand complex catalyze a number of different chemical transformations, including olefin polymerization reactions. The ligands, complexes formed with the ligands and compositions including the ligands are useful catalysts, depending on the reaction.

27 Claims, No Drawings

CATALYST LIGANDS, CATALYTIC METAL COMPLEXES AND PROCESSES USING SAME

This is a divisional of application Ser. No. 09/814,393, filed Mar. 21, 2001, now U.S. Pat. No. 6,316,663.

FIELD OF THE INVENTION

The present invention relates to new organic compounds (e.g., ligands), their metal complexes and compositions using those compounds; the invention also relates to the field of catalysis. In particular, this invention relates to new compounds which when combined with suitable metals or metal precursor compounds provide useful catalysts for various bond-forming reactions, including polymerizations and small molecule transformations. The invention also relates to combinatorial chemistry in that combinatorial techniques were used in connection with creating the ligands and testing compositions containing the ligands.

BACKGROUND OF THE INVENTION

Ancillary (or spectator) ligand-metal coordination complexes (e.g., organometallic complexes) and compositions are useful as catalysts, additives, stoichiometric reagents, monomers, solid state precursors, therapeutic reagents and drugs. Ancillary ligand-metal coordination complexes of this type can be prepared by combining an ancillary ligand with a suitable metal compound or metal precursor in a suitable solvent at a suitable temperature. The ancillary ligand contains functional groups that bind to the metal center(s), remain associated with the metal center(s), and therefore provide an opportunity to modify the steric, electronic and chemical properties of the active metal center(s) of the complex.

Certain known ancillary ligand-metal complexes and compositions are catalysts for reactions such as oxidation, reduction, hydrogenation, hydrosilylation, hydrocyanation, hydroformylation, polymerization, carbonylation, isomerization, metathesis, carbon-hydrogen activation, carbon-halogen activation, cross-coupling, Friedel-Crafts acylation and alkylation, hydration, dimerization, trimerization, oligomerization, Diels-Alder reactions and other transformations. See, e.g., U.S. Pat. Nos. 5,576,460 and 5,550,236, both of which are incorporated herein by reference.

One example of the use of these types of ancillary ligand-metal complexes and compositions is in the field of polymerization catalysis. In connection with single site catalysis, the ancillary ligand offers opportunities to modify the electronic and/or steric environment surrounding an active metal center. This allows the ancillary ligand to create possibly different polymers. Ancillary ligands and ancillary metal complexes that are similar to those disclosed herein have been discussed in WO 98/30609, incorporated herein by reference for all purposes. However, that application does not specifically disclose any of the ligands, complexes or compositions disclosed herein and does not disclose any method of making the ligands (i.e., the ancillary ligands) of this invention.

It is always a desire to discover new ancillary ligands, which upon coordination to a metal center or addition of a metal compound or precursor will catalyze or assist in catalysis of reactions differently from known ligand systems. This invention provides new ancillary ligands that may be used for coordination to a metal center or included in a composition with a metal or metal precursor compound. Upon coordination to the metal center or inclusion in the composition, such ligands influence the electronic and steric environment of the resulting coordination complex and may catalyze reactions differently, including more efficiently and selectively than known systems.

SUMMARY OF THE INVENTION

In a first aspect, the invention disclosed herein is a new ligand (i.e., an ancillary ligand), which can be characterized by the general formula:

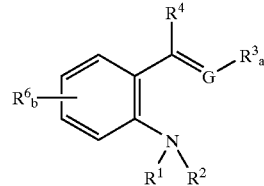

wherein each $R^1$, $R^2$, $R^3$, $R^4$ and $R^6$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure and/or $R^3$ and $R^4$ are joined together in a ring structure and/or $R^1$ and $R^6$ are joined together in a ring structure; and b is 0, 1, 2, 3 or 4. Where b is at least 2, two $R^6$ groups may be joined in a fused ring structure with the benzene ring in the backbone of the ligand. G is either oxygen or nitrogen. When G is oxygen, a is 0. When G is nitrogen, a is 1.

In a second aspect, this invention is a compound characterized by the general formula:

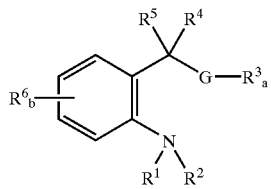

wherein each $R^1$, $R^2$, $R^3$, $R^4$, $R^5$ and $R^6$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure and/or $R^3$ and $R^4$ are joined together in a ring structure and/or $R^4$ and $R^5$ are joined together in a ring structure and/or $R^1$ and $R^6$ are joined together in a ring structure; G is either oxygen or nitrogen and a is either 1 or 2 depending on G; and b is 0, 1, 2, 3 or 4. When G is nitrogen and a is 2, the two $R^3$ groups may also join to form a ring structure.

This invention also relates to a novel method of making these new ligands. The general method of making these ligands is to start with a compound characterized by the general formula:

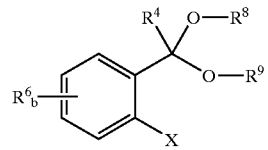

wherein $R^4$ and $R^6$ are as defined above and X is selected from the group consisting of chloro, bromo, iodo, triflate, tosylate and nonaflate; and $R^8$ and $R^9$ are independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. This compound is reacted with an amine characterized by the general formula $HNR^1R^2$, where $R^1$ and $R^2$ are as defined above. This provides ligands within the second aspect. Optionally, an acetyl or ketal functionality of the product is then hydroylzed, providing ligands within the first aspect. Thereafter, the product can be reacted with a primary or secondary amine to transform the ligand. Hydrogenation is thereafter an optional step. All steps may or may not be performed using parallel or high throughput or combinatorial methods.

In yet another aspect, this invention provides new metal-ligand complexes or compositions comprising the new ligands and a metal precursor. For catalysis, the ligands can be included in a composition including a suitable metal or metal precursor compound that can be of the form $ML_n$, where the composition has catalytic properties. Also, the ligands can be coordinated with a metal precursor to form metal-ligand complexes, which may be catalysts. Depending on the groups chosen for $R^1$, $R^2$ and $R^3$ in the ligand (i.e., prior to reaction with the metal precursor), the metal-ligand complexes can be characterized by one of many different general formulas depending on how the ligand attaches to or associates with the metal.

A further aspect of this invention provides for the novel ligands, compositions or complexes to be created and tested in a combinatorial manner. Thus, the ligands, compositions or complexes may be in an array with each ligand, composition or complex in a different region of a substrate. The number of ligands, compositions or complexes on a single substrate will vary according to the desired density, but will typically have at least 10 ligands, compositions or complexes on a single substrate.

These metal-ligand complexes or compositions catalyze polymerization and copolymerization reactions, particularly with monomers that are olefins, diolefms or otherwise acetylenically unsaturated. Other reactions that can be catalyzed include activation of and/or formation of H—Si, H—H, H—N, H—O, H—P, H—S, C—H, C—C, C=C, C≡C, C-halogen, C—N, C—O, C—S, C—P, and C—Si bonds. Specifically, such reactions include carbonylation, hydroformylation, hydroxycarbonylation, hydrocarbonylation, hydroesterification, hydrogenation, transfer hydrogenation, hydrosilylation, hydroboration, hydroamination, epoxidation, aziridation, reductive amination, C—H activation, insertion, C—H activation-insertion, C—H activation-substitution, C-halogen activation, C-halogen activation-substitution, C-halogen activation-insertion, cyclopropanation, alkene metathesis, alkene oligomerization, alkene polymerization, alkyne oligomerization, alkyne polymerization, CO-alkene co-oligomerization, CO-alkene co-polymerization, CO-alkyne co-oligomerization and CO-alkyne co-polymerization.

Thus, in another aspect of the invention, a polymerization process is disclosed for olefins, diolefins and other acetylenically unsaturated compounds. The polymerization process involves contacting monomers to the catalyst compositions or to the coordination complexes of this invention under polymerization conditions. The catalyst compositions or the coordination complexes may be active catalysts themselves or make be activated with a known activating technique or compound. The polymerization process can be continuous, batch or semi-batch and can be homogeneous or heterogeneous, as discussed further below.

Further aspects of this invention will be evident to those of skill in the art upon review of this specification.

DETAILED DESCRIPTION OF THE INVENTION

The inventions disclosed herein are new ligands that may be combined with metals or metal precursor compounds to form coordination complexes or compositions of matter, which are useful as catalysts for chemical reactions. The invention also is for processes for making the ligand, processes for making the metal complexes and processes for using the resultant composition or coordination complex as a catalyst. Finally, the invention provides these new compounds and compositions and complexes in an array format.

As used herein, the phrase "characterized by the formula" is not intended to be limiting and is used in the same way that "comprising" is commonly used. The term "independently selected" is used herein to indicate that the R groups, e.g., $R^1$, $R^2$, $R^3$, $R^4$, and $R^5$ can be identical or different (e.g. $R^1$, $R^2$, $R^3$, $R^4$, and $R^5$ may all be substituted alkyls or $R^1$ and $R^2$ may be a substituted alkyl and $R^3$ may be an aryl, etc.). A named R group will generally have the structure that is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

"Substituted alkyl" refers to an alkyl as just described in which one or more hydrogen atom to any carbon of the alkyl is replaced by another group such as a halogen, aryl, substituted aryl, cycloalkyl, substituted cycloalkyl, and combinations thereof. Suitable substituted alkyls include, for example, benzyl, trifluoromethyl and the like.

The term "heteroalkyl" refers to an alkyl as described above in which one or more hydrogen atoms to any carbon of the alkyl is replaced by a heteroatom selected from the group consisting of N, O, P, B, S, Si, Se and Ge. The bond between the carbon atom and the heteroatom may be saturated or unsaturated. Thus, an alkyl substituted with a heterocycloalkyl, substituted heterocycloalkyl, heteroaryl, substituted heteroaryl, alkoxy, aryloxy, boryl, phosphino, amino, silyl, thio, or seleno is within the scope of the term heteroalkyl. Suitable heteroalkyls include cyano, benzoyl, 2-pyridyl, 2-furyl and the like.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

"Substituted cycloalkyl" refers to cycloalkyl as just described including in which one or more hydrogen atom to any carbon of the cycloalkyl is replaced by another group such as a halogen, alkyl, substituted alkyl, aryl, substituted aryl, cycloalkyl, substituted cycloalkyl, heterocycloalkyl, substituted heterocycloalkyl, heteroaryl, substituted heteroaryl, alkoxy, aryloxy, boryl, phosphino, amino, silyl, thio, seleno and combinations thereof. Suitable substituted cycloalkyl radicals include, for example, 4-dimethylaminocyclohexyl, 4,5-dibromocyclohept4-enyl, and the like.

The term "heterocycloalkyl" is used herein to refer to a cycloalkyl radical as described, but in which one or more or all carbon atoms of the saturated or unsaturated cyclic radical are replaced by a heteroatom such as nitrogen, phosphorous, oxygen, sulfur, silicon, germanium, selenium, or boron. Suitable heterocycloalkyls include, for example, piperazinyl, morpholinyl, tetrahydropyranyl, tetrahydrofuranyl, piperidinyl, pyrrolidinyl, oxazolinyl and the like.

"Substituted heterocycloalkyl" refers to heterocycloalkyl as just described including in which one or more hydrogen atom to any atom of the heterocycloalkyl is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heterocycloalkyl radicals include, for example, N-methylpiperazinyl, 3-dimethylaminomorpholinyl and the like.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone or oxygen as in diphenylether or nitrogen in diphenylamine. The aromatic ring(s) may include phenyl, naphthyl, biphenyl, diphenylether, diphenylamine and benzophenone among others. In particular embodiments, aryls have between 1 and 200 carbon atoms, between 1 and 50 carbon atoms or between 1 and 20 carbon atoms.

"Substituted aryl" refers to aryl as just described in which one or more hydrogen atom to any carbon is replaced by one or more functional groups such as alkyl, substituted alkyl, cycloalkyl, substituted cycloalkyl, heterocycloalkyl, substituted heterocycloalkyl, halogen, alkylhalos (e.g., $CF_3$), hydroxy, amino, phosphido, alkoxy, amino, thio and both saturated and unsaturated cyclic hydrocarbons which are fused to the aromatic ring(s), linked covalently or linked to a common group such as a methylene or ethylene moiety. The linking group may also be a carbonyl such as in cyclohexyl phenyl ketone.

The term "heteroaryl" as used herein refers to aromatic rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as a methylene or ethylene moiety. The common linking group may also be a carbonyl as in phenyl pyridyl ketone. As used herein, rings such as thiophene, pyridine, isoxazole, phthalimide, pyrazole, indole, furan, etc. or benzo-fused analogues of these rings are defined by the term "heteroaryl."

"Substituted heteroaryl" refers to heteroaryl as just described including in which one or more hydrogen atoms to any atom of the heteroaryl moiety is replaced by another group such as a halogen, alkyl, substituted alkyl, aryl, substituted aryl, heteroaryl, substituted heteroaryl, alkoxy, aryloxy, boryl, phosphino, amino, silyl, thio, seleno and combinations thereof. Suitable substituted heteroaryl radicals include, for example, 4-N,N-dimethylaminopyridine.

The term "alkoxy" is used herein to refer to the —$OZ^1$ radical, where $Z^1$ is selected from the group consisting of alkyl, substituted alkyl, cycloalkyl, substituted cycloalkyl, heterocylcoalkyl, substituted heterocycloalkyl, silyl groups and combinations thereof as described herein. Suitable alkoxy radicals include, for example, methoxy, ethoxy, benzyloxy, t-butoxy, etc. A related term is "aryloxy" where $Z^1$ is selected from the group consisting of aryl, substituted aryl, heteroaryl, substituted heteroaryl, and combinations thereof. Examples of suitable aryloxy radicals include phenoxy, substituted phenoxy, 2-pyridinoxy, 8-quinalinoxy and the like.

As used herein the term "silyl" refers to the —$SiZ^1Z^2Z^3$ radical, where each of $Z^1$, $Z^2$, and $Z^3$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein the term "boryl" refers to the —$BZ^1Z^2$ group, where each of $Z^1$ and $Z^2$ is independently selected from the group consisting of alkyl, substituted alkyl, cycloalkyl, heterocycloalkyl, heterocyclic, aryl, substituted aryl, heteroaryl, substituted heteroaryl, alkoxy, aryloxy, amino, silyl and combinations thereof.

As used herein, the term "phosphino" refers to the group —$PZ^1Z^2$, where each of $Z^1$ and $Z^2$ is independently selected from the group consisting of hydrogen, substituted or unsubstituted alkyl, cycloalkyl, heterocycloalkyl, heterocyclic, aryl, heteroaryl, silyl, alkoxy, aryloxy, amino and combinations thereof.

The term "amino" is used herein to refer to the group —$NZ^1Z^2$, where each of $Z^1$ and $Z^2$ is independently selected from the group consisting of hydrogen; alkyl, substituted alky, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "thio" is used herein to refer to the group —$SZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof.

The term "seleno" is used herein to refer to the group —$SeZ^1$, where $Z^1$ is selected from the group consisting of hydrogen; alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, silyl and combinations thereof The term "saturated" refers to lack of double and triple bonds between atoms of a radical group such as ethyl, cyclohexyl, pyrrolidinyl, and the like.

The term "unsaturated" refers to the presence one or more double and triple bonds between atoms of a radical group such as vinyl, acetylenyl, oxazolinyl, cyclohexenyl, acetyl and the like.

The new ligands of this invention can be characterized by either of the general formulas:

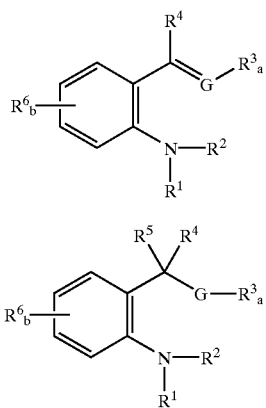

wherein each $R^1$, $R^2$, $R^3$, $R^4$, $R^5$ and $R^6$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure and/or $R^3$ and $R^4$ are joined together in a ring structure and/or $R^4$ and $R^5$ are joined together in a ring structure; and b is 0, 1, 2, 3 or 4. G is an element selected from the group consisting of oxygen and nitrogen. In connection with structure I, a is 0 when G is oxygen and a is 1 when G is nitrogen. In connection with structure II, a is 1 when G is oxygen and a is 2 when G is nitrogen. Also in connection with structure II, when a is 2, the two $R^3$ groups may be the same or different and optionally may be joined together in a ring structure.

In more specific embodiments, $R^1$ and $R^2$ are independently selected from a group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl and silyl. Specific examples of $R^1$ and $R^2$ are hydrogen, methyl, ethyl, propyl, butyl, cyclopentyl, cylcohexyl, cyclooctyl, phenyl, naphthyl, benzyl, trimethylsilyl, and the like. In those embodiments where $R^1$ and $R^2$ are joined together in a ring structure, the ring (including $R^1$, $R^2$ and N) has from 3 to 15 non-hydrogen atoms as part of the backbone of the ring. Specific examples of $R^1$ and $R^2$ together are ethylene (giving a 3-member ring), propylene (giving a 4-membered ring), butylene (giving a 5-membered ring), 3-oxopentylene (giving a 6-membered ring) and the like.

In a preferred embodiment, $R^1$ is a substituted or unsubstituted phenyl and $R^2$ is hydrogen. If $R^1$ is a substituted phenyl, there may be 1, 2, 3, 4 or 5 substituents attached to carbon atoms in the phenyl ring. Each of these substituents may be independently selected from the group consisting of alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. More preferably, there are 1, 2 or 3 substituents on the substituted phenyl and the substituents are selected from the group consisting of chloro, fluoro, iodo, bromo, methyl, ethyl, propyl, butyl, cyclopentyl, cylcohexyl, cyclooctyl, phenyl, naphthyl, benzyl, trimethylsilyl and isomers thereof.

More specifically, $R^3$ is selected from a group consisting of hydrogen, alkyl, substituted alkyl, cycloalkyl, substituted cycloalkyl, heterocycloalkyl, substituted heterocycloalkyl, aryl, substituted aryl, heteroaryl, substituted heteroaryl, alkyloxy, aryloxy, amino, silyl, boryl and phosphino. Specific examples of $R^3$ are methyl, ethyl, propyl, butyl, cyclohexyl, cyclopropyl, cycloheptyl, t-butyl, phenyl, biphenyl, naphthyl, benzyl, pyridyl, furyl, quinolyl, morpholinyl, cyano, methoxy, ethoxy, t-butoxy, phenoxy, benzyloxy, dimethylamino, diethylamino, diphenylarnino, phenylmethylamino, benzylmethylamino, trimethylsilyl, dimethyl-t-butylsilyl, triphenylsilyl, triethoxysilyl, dimethylboryl, diphenylboryl, diphenoxyboryl, 1,2-dioxyphenylboryl, 2,2'-biphenoxyboryl, 2,2'-dinaphthoxyboryl, diphenylphosphino, dibutylphosphino, dimethylphosphino, dicyclohexylphosphino, dicylcyclopentylphosphino, nitro, and methylphenylphosphino.

Most preferably, $R^3$ is benzyl or a substituted or unsubstituted phenyl. Where $R^3$ is a substituted phenyl and there are 1, 2, 3, 4 or 5 substituents on the phenyl ring, with each of said substituents independently selected from the group consisting of alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, hydroxy, halogens, alkoxy, aryloxy, silyl, boryl, phosphino, amino, thio, seleno, and combinations thereof. Preferably in those embodiments there are 1, 2 or 3 substituents on the substituted phenyl and the substituents are selected from the group consisting of chloro, fluoro, iodo, bromo, methyl, ethyl, propyl, butyl, cyclopentyl, cylcohexyl, cyclooctyl, phenyl, naphthyl, benzyl, trimethylsilyl and isomers thereof Also in more specific embodiments, $R^4$ is selected from the group consisting of hydrogen, alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkyloxy, aryloxy, boryl, amino and silyl. In yet other embodiments, $R^4$ may be selected from the group consisting of hydrogen, alkyl, aryl and cycloalkyl. Specific examples of $R^4$ are hydrogen, methyl, ethyl, propyl, butyl, cyclopentyl, cylcohexyl, cyclooctyl, phenyl, naphthyl, benzyl, pyridyl, furyl, morpholino, methoxy, ethoxy, butoxy, phenoxy, benzyloxy, dimethylboryl, diphenylboryl, methylphenylboryl, dimethylamino, diethylamino, diphenylamino, dibenzylamino, trimethylsilyl, triethoxysilyl, triphenylsilyl, triphenoxysilyl, dimethyl-t-butylsilyl, and the like.

In some embodiments where $R^3$ and $R^4$ are joined together in a ring structure, the ring (including $R^3$, $R^4$, G and C) has from 4 to 15 non-hydrogen atoms as part of the backbone of the ring. In connection with structure I, G is nitrogen and a is 1 and $R^3$ is selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino and combinations thereof. Specific examples of $R^3$ and $R^4$ together are ethylene (giving a 4-membered ring), butylene (giving a 6-membered ring), bicyclooctyl, bicyclohexyl, 2,2'-biphenyl (giving a dibenzo fused 6-membered ring), 2,2'-binaphthyl (giving a dinaphtho fused 6-membered ring), 2,2'-biphenoxy (giving a 8-membered ring), 2,2'-dinaphthoxy (giving a 8-membered ring) and diethoxy (giving a 6-membered ring).

Also in more specific embodiments, $R^6$ is selected from the group consisting of electron withdrawing and electron donating groups and b is 0, 1, 2, 3 or 4. $R^6$ can take any open position on the benzene ring that helps form the backbone of the ligand. More specifically, $R^6$ may be chosen from the group consisting of alkyl, substituted alkyl, cycloalkyl, substituted cycloalkyl, heterocycloalkyl, substituted heterocycloalkyl, aryl, substituted aryl, heteroaryl, substituted heteroaryl, silyl, amino, alkoxy, aryloxy, phosphino, boryl, transition metals, halogens and combinations thereof. Specific examples of $R^6$ include methyl, ethyl, propyl, t-butyl, phenyl, cyano, acetyl, benzyl, nitro, dimethylamino, diethylamino, methylphenylamino, benzylmethylamino, trimethylsilyl, dimethylboryl, diphenylboryl, methylphenylboryl, dimethoxyboryl, chromium tricarbonyl, ruthenium tricarbonyl, and cyclopentadienyl iron. Optionally, two or more $R^5$ groups combine to form a fused ring structure with the aromatic group that forms a part of the ligand backbone. The additional fused ring may or may not contain a heteroatom. Examples of the aromatic group that is part of the backbone as combined with two or more $R^6$ groups that have formed a fused ring are naphthalene, quinoline, indole and the like.

In connection with structure II, $R^5$ is present. $R^5$ may be selected from the group consisting of hydrogen, alkyl, substituted alkyl, cycloalkyl, substituted cycloalkyl, heteroalkyl, aryl, substitute aryl, heteroaryl, substituted heteroaryl, alkoxy, aryloxy, amino and silyl. In more specific embodiments, $R^5$ is selected from the group consisting of hydrogen, methyl, ethyl, propyl, butyl, cyclopentyl, cylcohexyl, cyclooctyl, phenyl, naphthyl, benzyl, pyridyl, furyl, morpholino, methoxy, ethoxy, butoxy, phenoxy, benzyloxy, dimethylboryl, diphenylboryl, methylphenylboryl, dimethylamino, diethylamino, diphenylamino, dibenzylamino, trimethylsilyl, triethoxysilyl, triphenylsilyl, triphenoxysilyl, dimethyl-t-butylsilyl, and the like. Also in connection with structure II, $R^5$ may be joined in a ring structure with G and $R^3$ in the backbone of the ring. Such a ring will have at least four atoms in the backbone of the ring. In the case of a ring, G can be oxygen or nitrogen and $R^3$ forms a methylene bridge to $R^5$. In this case, $R^5$ is alkoxy, so that the ring has at least five atoms in the backbone of the ring, as follows: C—O—$(CH_2)_x$—$CH_2$—O, with the last O being bonded to the first C and x denoting the length of the alkyl portion of $R^5$. In yet other embodiments, $R^4$ and $R^5$ are joined in a ring structure, having at least three atoms in the backbone. Where $R^4$ and $R^5$ are joined together in a ring structure, the ring (including $R^4$, $R^5$ and C) has from 3 to 15 non-hydrogen atoms as part of the backbone of the ring. Specific examples of $R^4$ and $R^5$ together are ethylene (giving a 3-member ring), propylene (giving a 4-membered ring), butylene (giving a 5-membered ring), 3-oxopentylene (giving a 6-membered ring) and the like.

The ligands of this invention may be synthesized using an aryl amination reaction. The synthesis can be carried out in solution phase or solid phase (using organic or inorganic supports). For solid-phase synthesis, the ligands may be left on the support and used with metal added metal complexes as heterogeneous catalysts. Alternatively, the ligands can be cleaved either before or after reaction with a metal precursor and then used as a homogeneous catalyst. One the general route for synthesis of the ligands of this invention is shown below in scheme 1:

Scheme 1

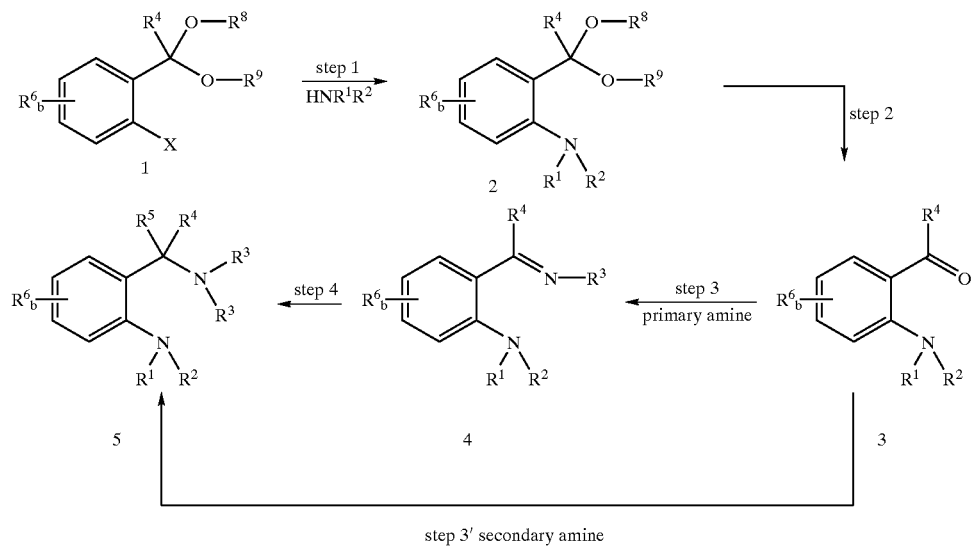

As shown in scheme 1, compounds 3 and 4 are within general structure I above, and compounds 2 and 5 are within general structure II above. Generally, the synthesis employs an aryl amination reaction to attach the nitrogen group to the benzene ring at the appropriate location. Following scheme 1, above, step 1 is an aryl amination reaction starting with a compound characterized by the general formula:

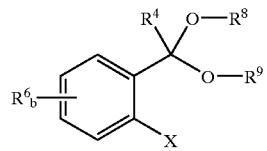

wherein $R^4$ and $R^6$ are as defined above and X is selected from the group consisting of chloro, bromo, iodo, triflate, nonaflate, alkyl sulfonates, aryl sulfonates and tosylate; and $R^8$ and $R^9$ are independently selected from the group consisting of alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. Compounds of this type can be purchased from Aldrich Chemical or prepared using known techniques. See, e.g., Greene, Theodra W. and Wuts, Peter G. M., Protecting Groups in Organic Synthesis, $2^{nd}$ Edition (John Wiley & Sons, New York, N.Y. 1991).

The aryl amination reaction could also start with other compounds, such as those characterized by the following general formulas in the following Schemes 2 and 3:

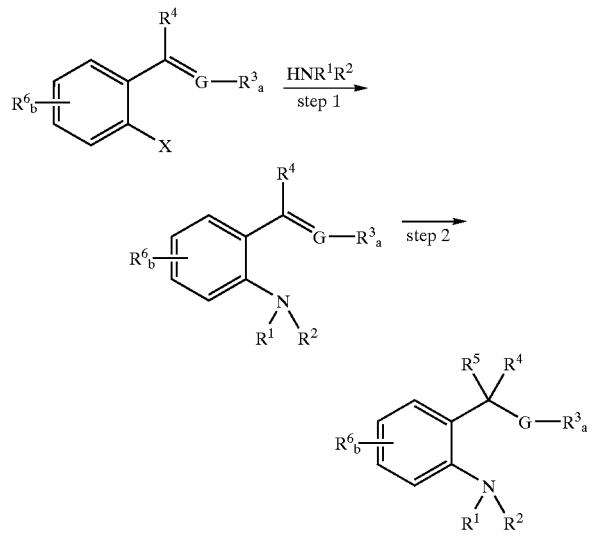

Scheme 2

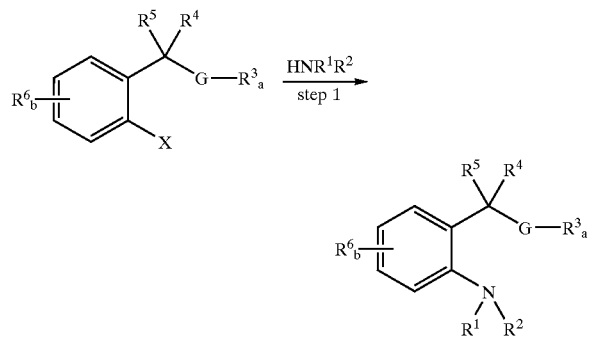

Scheme 3

In these schemes, the variable groups have the previously indicated meanings.

Step 1 is any scheme is the aryl amination reaction. This reaction uses an amine that can be characterized by the general formula $HNR^1R^2$, where $R^1$ and $R^2$ are as defined above. This aryl amination reaction is typically performed using a catalyst that comprises known or possibly new metal and ligand catalyst compositions. For example, the catalyst may be characterized by the general formula M'/L', where M' is a complex that contains a metal selected from the group consisting of late transition metals, preferably a Group 10 metal such as Pd, Ni or Pt. M' is any homogeneous or heterogeneous metal precursor catalyst or catalyst, L' is a ligand that may be selected from the group consisting of phosphine or nitrogen ligands. L' may be monodentate, bidentate, tridentate, hemi-labile, unsubstituted or substituted, supported or unsupported, water-soluble or insoluble, soluble or insoluble in organic solvents including fluorinated solvents. The reaction can take place at known conditions, such as a temperature of from room temperature to about 150° C. Aryl amination reactions are described in U.S. Pat. No. 5,576,460 herein incorporated by reference.

Referring now to scheme 1, the second step of the reaction converts compound 2 to compound 3 by hydrolysis of an acetal or ketal functionality. This reaction can be performed by one of skill in the art. See, e.g., Greene, Theodra W. and Wuts, Peter G. M., Protecting Groups in Organic Synthesis, $2^{nd}$ Edition (John Wiley & Sons, New York, N.Y. 1991), herein incorporated by reference.

Thereafter in scheme 1, compound 3 can be reacted with a primary or secondary amine for transform the ligand. The primary or secondary amine in step 3 or 3' can be characterized by the general formula $H_{3-a}NR^3{}_a$, where $R^3$ is as defined above and a is 1 for a primary amine and a is 2 for a secondary amine. A primary amine provides compound 4 in above scheme 1 following step 3. A secondary amine in the presence of a hydride source provides a compound within above general ligand structure II in above scheme 1 following step 3'. If a primary amine is employed, hydrogenation is thereafter an optional fourth step in scheme 1.

Once the desired ligand is formed, it may be combined with a metal atom, ion, compound or other metal precursor compound. In many applications, the ligands of this invention will be combined with such a metal compound or precursor and the product of such combination is not determined, if a product forms. For example, the ligand may be added to a reaction vessel at the same time as the metal or metal precursor compound along with the reactants. The metal precursor compounds may be characterized by the general formula $M(L)_n$ where M is a metal selected from the group consisting of Groups 3, 4, 5, 6, 7, 8, 9 and 10 of the Periodic Table of Elements. In more specific embodiments, M is selected from the group consisting of Ti, Zr, Hf, V, Ta, Cr, W, Mo, Ru, Co, Ni, Pd, Fe, Mn, and Pt. L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is a charged ligand, L is selected from the group consisting of hydrogen halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, acetoxy, silyl, boryl, phosphino, amino, thio, seleno, and combinations thereof. When L is a neutral ligand, L is selected from the group consisting of carbon monoxide, isocyanide, dibenzylideneacetone, nitrous oxide, $PA_3$, $NA_3$, $OA_2$, $SA_2$, $SeA_2$, and combinations thereof, wherein each A is independently selected from a group consisting of alky, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino. Specific examples of suitable metal precursor compounds include $Pd(dba)_2$ (dba=dibenylideneacetone), $Pd(OAc)_2$ (Ac=acetate) and the like. In this context, the ligand to metal precursor compound ratio is in the range of about 0.01:1 to about 100:1, more preferably in the range of about 0.5:1 to about 20:1.

In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be a catalyst.

Depending on the substituents chosen for the ligand prior to reaction with the metal precursor compound, the metal complexes may be characterized by any of the following general formulas. For general ligand structure 1, the possible metal complexes formed include:

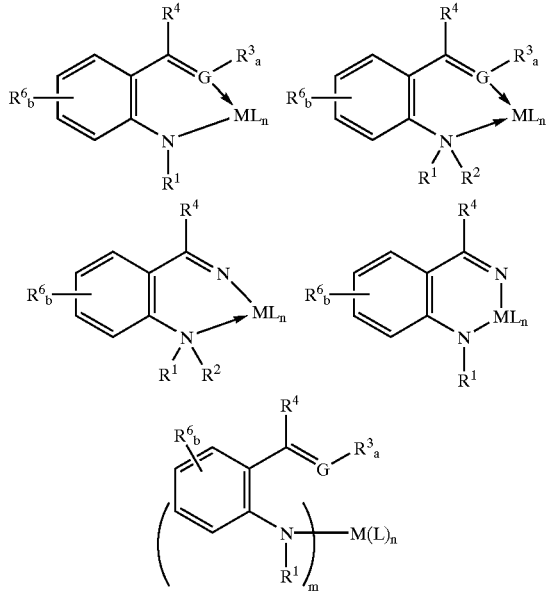

For general ligand structure II, the possible metal complexes formed include:

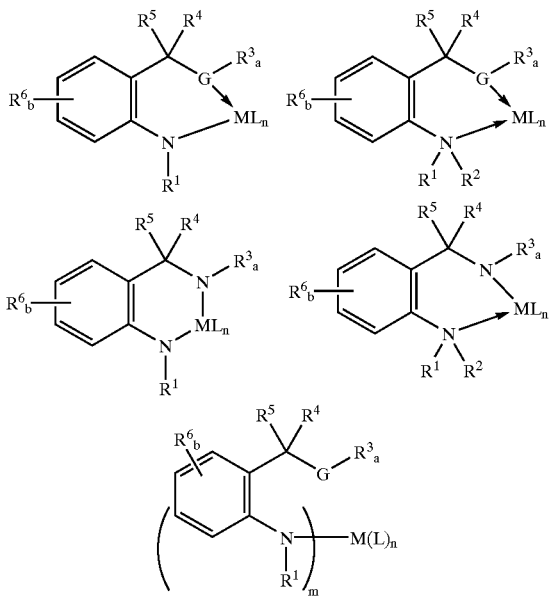

In each of these formulas, each $R^1$, $R^2$, $R^3$, $R^4$, $R^5$, $R^6$, G, a and b are as defined above; and M is a transition metal selected from the group consisting of Groups 3, 4, 5, 6, 7, 8, 9 and 10 of the Periodic Table of Elements. Selection of the metal is most preferably dependent on whether the ligand is monoanionic or dianionic. In more specific embodiments, M is selected from the group consisting of V, Ta, Cr, W, Mo, Ru, Co, Ni, Pd, Fe, Mn and Pt.

L is independently each occurrence, a neutral and/or charged ligand. Generally, L is a ligand chosen from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof. When L is a charged ligand, L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. When L is a neutral ligand, L is selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino.

n is the number 0, 1, 2, 3, 4, and 5. Additionally, m is 1, 2, 3, or 4. M can be neutral, cationic or anionic. In this form, the ligands of this invention that bind to a metal via the N atoms with dative bonds are shown with arrows and covalent binding is shown with a line. Coordination modes described above may or may not depend on the nature of ligands L on the metal M, and for a given ligand L, the coordination modes may switch from one to another at different stages of a catalytic cycle.

These transition metal-ligand complexes or metal/ligand compositions of matter catalyze reactions involving activation of and formation of bonds between H—Si, H—H, H—N, H—O, H—P, H—S, C—H, C—C, C=C, C=C, C≡C, C-halogen, C—N, C—O, C—S, C—P, and C—Si. Specifically, such reactions include carbonylation, hydroformylation, hydroxycarbonylation, hydrocarbonylation, hydroesterification, hydrogenation, hydrosilylation, hydroboration, hydroamination, epoxidation, aziridation, reductive amination, C—H activation, insertion, C—H activation-insertion, C—H activation-substitution, C-halogen activation, C-halogen activation-substitution, C-halogen activation-insertion, alkene metathesis, polymerization, alkene oligomerization, alkene polymerization, alkyne oligomerization, alkyne polymerization, co-polymerization, CO-alkene co-oligomerization, CO-alkene co-polymerization, CO-alkyne co-oligomerization and CO-alkyne co-polymerization. These reactions may occur at previously known conditions (or possibly novel conditions). Moreover, these reactions may be homogeneous or heterogeneous. In the case of heterogeneous reactions, the ligands may be supported, with or without the metal coordinated, on an organic or inorganic support. Suitable supports include silicas, aluminas, zeolites, polyethyleneglycols, polystyrenes, polyesters, polyamides, peptides and the like.

Polymerization catalysis with the compositions and metal complexes of this invention is a particularly effective process. In particular, the complexes and compositions of this invention are active catalysts also for the polymerization of olefins, possibly in combination with an activator or activating technique. When an activator or activating technique is used, those of skill in the art may use alumoxanes, strong Lewis acids, compatible noninterfering activators and combinations of the foregoing. The foregoing activators have been taught for use with different metal complexes in the following references, which are hereby incorporated by reference in their entirety: U.S. Pat. Nos. 5,599,761, 5,616, 664, 5,453,410, 5,153,157, 5,064,802, and EP-A-277,004. Preferred activators include methylalumoxane, trimethylaluminum, $AgBF_4$, AgBPh4, $NaBAr'_4$, $H(OEt_2)_2$ $BAr'_4$ and the like (where Ar' is a substituted aromatic, like perfluorophenyl or $3,5-(CF_3)_2(C_6H_3)$).

Ratios of neutral complex to activator are on the order of 1 to 1000 to 1000 to 1. A scavenger can also be used with this invention. Scavengers useful herein include metal complexes, alumoxanes, aluminum alkyls and the like. Other additives that are standard for polymerization reactions can be used.

The catalysts herein may be used to polymerize ethylenically or acetylenically unsaturated monomers having from 2 to 20 carbon atoms either alone or in combination. Monomers include $C_2$ to $C_{20}$ α-olefins such as ethylene, propylene, I -butene, I-hexene, 1-octene, 4-mtheyl-1-pentene, styrene and mixtures thereof.

The compounds and catalysts of this invention usefully polymerize functionalized monomers, such as acetates and acrylates. Novel polymers, copolymers or interpolymers may be formed having unique physical and/or melt flow properties. Such novel polymers can be employed alone or with other polymers in a blend to form products that may be molded, cast, extruded or spun. End uses for the polymers made with the catalysts of this invention include films for packaging, trash bags, foams, coatings, insulating devices and household items. Also, such finctionalized polymers are useful as solid supports for organometallic or chemical synthesis processes.

Polymerization can be carried out in the Ziegler-Natta or Kaminsky-Sinn methodology, including temperatures of from 0° C. to 400° C. and pressures from atmospheric to 3000 atmospheres. Suspension, solution, slurry, gas phase or high-pressure polymerization processes may be employed with the catalysts and compounds of this invention. Such processes can be run in a batch or continuous mode. Examples of such processes are well known in the art. A support for the catalyst may be employed, which may be alumina, silica or a polymers support. Methods for the preparation of supported catalysts are known in the art. Slurry, suspension, solution and high-pressure processes use a suitable solvent as known to those skilled in the art.

The ligands, metal complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. U.S. Pat. No. 5,776,359 and WO 98/03521, both of which are incorporated herein by reference generally disclose combinatorial methods. In this regard, the ligands, complexes or compositions may be prepared and/or tested in rapid serial and/or parallel fashion, e.g., in an array format. When prepared in an array format, for example, the ligands may be take the form of an array comprising a plurality of compounds wherein each compound can be characterized by either of the general formulas:

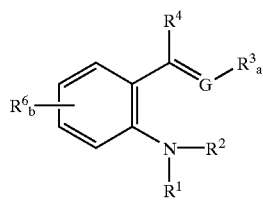

I

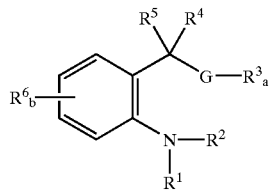

II wherein each $R^1$, $R^2$, $R^3$, $R^4$ $R^5$ and $R^6$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure and/or $R^3$ and $R^4$ are joined together in a ring structure; G is either oxygen or nitrogen. In connection with structure I, a is 0 or 1 depending on G. In connection with structure II, a is 1 or 2 depending on G. Also, b is 0, 1, 2, 3 or 4.

In such a combinatorial array, typically each of the plurality of compounds has a different composition and each compound is at a selected region on a substrate such that each compound is isolated from the other compounds. This isolation can take many forms, typically depending on the substrate used. If a flat substrate is used, there may simply be sufficient space between regions so that there cannot be interdiffusion between compounds. As another example, the substrate can be a microtiter or similar plate having wells so that each compound is in a region separated from other compounds in other regions by a physical barrier.

The array typically comprises at least 10 compounds, complexes or compositions each having a different chemical formula, meaning that there must be at least one different atom or bond differentiating the plurality in the array. In other embodiments, there are at least 25 compounds, complexes or compositions on or in the substrate each having a different chemical formula. In still other embodiments, there are at least 50 or 96 or 124 compounds, complexes or compositions on or in the substrate each having a different chemical formula. Because of the manner of forming combinatorial arrays, it may be that each compound, complex or composition is not pure. Typically, plurality of compounds are at least 50% pure within said regions.

The catalytic performance (activity and selectivity) of the ligands of this invention in combination with a suitable metal precursor or metal-ligand coordination complexes of this invention can be tested in a combinatorial or high throughput fashion. For any of the listed transformation, thin layer chromatography (TLC) in combination with imaging technology may be employed. TLC is well known in the art, see for example Vol. 1, *Thin-Layer Chromatography, Reagents & Detection Methods,* Jork et al. (VCH Publishers, New York, N.Y. 1990). Polymerizations can also be performed in a combinatorial fashion, see, e.g., commonly owned provisional U.S. patent application Ser. No. 60/096, 603, filed Aug. 13, 1998 (having attorney docket no. 65304-010), herein incorporated by reference. High throughput screening can also be performed optically and in parallel, for example, as disclosed in commonly owned U.S. patent applications Ser. No. 09/067,448, filed Apr. 2, 1998, 08/947, 085, filed Oct. 8, 1997, and 08/946,135, filed Oct. 7, 1997, each of which is incorporated by reference.

EXAMPLES

General: All reactions were performed under argon atmosphere in oven-dried glass Schlenk tubes using standard Schlenk techniques. All aryl halides, all amines, sodium t-butoxide, bis(dibenzylideneacetone)palladium, and all solvents used were purchased from commercial sources and used as such. All solvents used were of the anhydrous, Sure-Seal® grade. Column chromatography was performed using commercially available Silica Gel 60 (particle size: 0.063–0.100 mm), hexanes and ethyl acetate. GCMS analyses were conducted on a Hewlett-Packard 5890 instrument. $^1$H, and $^{13}$C spectra were obtained using a Bruker 300 MHz FT-NMR spectrometer. Chemical shifts in $^1$H and $^{13}$C NMR spectra were calibrated with reference to the chemical shift of residual protiated solvent. Elemental analyses were performed by E & R Microanalytical Laboratory Inc., NJ. Ligand A was used for the aryl amination reaction and is 2-(2'-dicyclohexylphosphinophenyl)-2-methyl-1,3-dioxolane having the following structure:

Ligand A

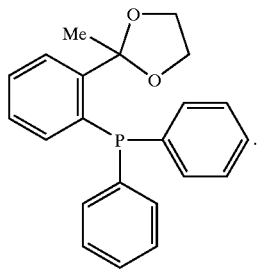

Synthesis and use of ligand A is disclosed in detail in commonly owned and copending U.S. patent application Ser. No. 09/062,128 filed Apr. 17, 1998 and incorporated herein by reference. Also U.S. provisional patent application Ser. No. 60/095,612, filed Aug. 6, 1998 and herein incorporated by reference discloses other ligands that can be used in the aryl amination reaction.

The following ligands shown in structural form below are referred to using the code given below each structure:

1a

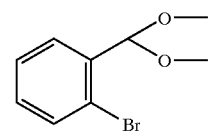

1b

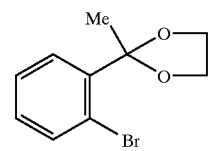

2b-1

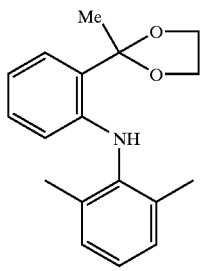

2b-2

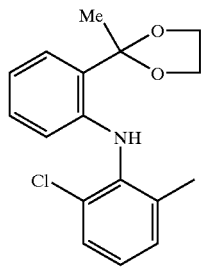

2b-3

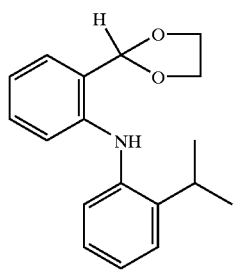

3a-1

3a-2

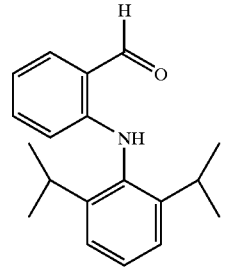

4a-1

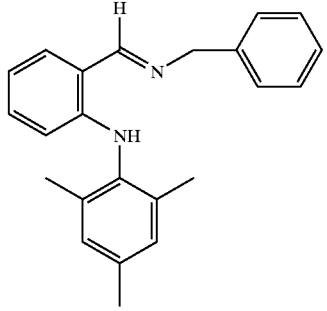

-continued

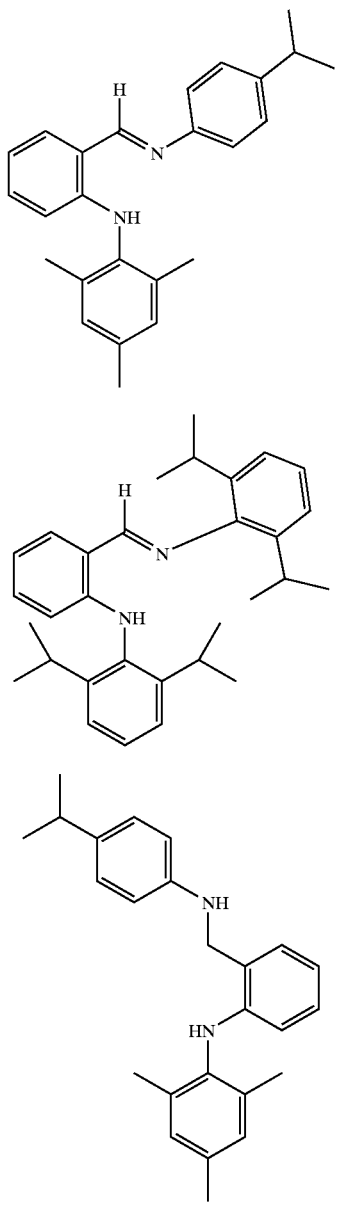

Example 1: 2-Bromo-1(dimethoxymethyl)benzene (1a). To a 500 mL round bottom flask equipped with a reflux condenser were added 2-bromobenzaldehyde (102. 5 g, 0.554 mol, Aldrich), trimethyl orthoformate (64.9 mL, 0.594 mol, Aldrich), 10-camphor sulfonic acid (1.25 g, 5.40 mmol, Aldrich), and methanol (100 mL). The reaction was heated at reflux for 14 hrs and concentrated in vacuo. The residue was taken up in 500 mL of ether, washed with 200 mL each of sat. aqueous sodium bicarbonate, water, and sat. aqueous NaCl, dryed over anhydrous sodium sulfate, filtered and concentrated in vacuo. The crude product was distilled through a 27 cm Vigrew column (b.p. 78–82° C./1.2 nmHg), affording a clear colorless oil (120.8 g, 94%). 1H-NMR (300 MHz, CDCl3) δ 3.37 (s, 6H), 5.54 (s, 1H), 7.18 (dt, 1H, J=1.7, 8.1 Hz), 7.31 (dt, 1H, J=1.2, 7.5 Hz), 7.54 (dd, 1H, J=1.2, 8.1 Hz), 7.59 (dd, 1H, J=1.7, 7.5 Hz). Mass spectrum (EI+) m/e 230, 232 (M+), 199, 201 (bp).

Example 2: 2-[2'-(2,6-Dimethylanilino)phenyl]-2-methyl-1,3-dioxolane (2b-1): A mixture of 2-(2'-bromophenyl)-2-methyl- 1,3-dioxolane (362 mg, 1.49 mmol), 2,6-dimethylaniline(189 mg, 1.56 mmol), NaO$^t$Bu (172 mg, 1.79 mmol), Pd(dba)$_2$ (17 mg, 0.03 mmol), ligand A (21 mg, 0.06 mmol) in toluene (4 mL) was heated to 105° C. for 4.5 hours. The reaction was cooled to room temperature, taken up in diethyl ether (125 mL), washed with water (2×30 mL) and brine (30 mL), dried over MgSO$_4$, filtered and concentrated under vacuum. The crude product was purified by column chromatography on silica gel using hexane (or hexanes: ethyl acetate) as the eluent to afford compound 2b-1, after drying under vacuum, as an off-white solid (yield: 391 mg, 93 %). $^1$H NMR (CDCl$_3$): δ 7.41 (dd, 1H, J=7.8, 1.8 Hz, ArH), 7.13–6.99 (m, 4H, ArH), 6.70 (dt, 1H, J =7.5, 1.2 Hz, ArH), 6.15 (dd, 1H, J=7.8, 0.9, ArH), 4.12 (m, 2H, O—CH—CH—O), 3.93 (m, 2H, O—CH—CH—O), 2.18 (s, 6H, Ar—CH$_3$), 1.84 (s, 3H, CH$_3$). $^{13}$C NMR (CDCl$_3$): δ 143.5, 138.6, 135.2, 129.1, 128.5, 126.3, 125.6, 125.2, 117.3, 112.6, 109.8, 64.1, 24.1, 20 18.3. Anal. for C$_{18}$H$_{21}$NO$_2$; Calcd: C, 76.29; H, 7.47; N, 4.94; Found: C, 75.86; H, 7.46; N, 4.89.

Example 3: 2-[2'(2-Chloro-6-methylanilinophenyl)]-2-methyl-1,3-dioxolane (2b-2): A Compound 2b-2 (381 mg, 96 % yield) was obtained as a colorless solid from the reaction of 2-(2'-bromophenyl)-2-methyl-1,3-dioxolane (318 mg, 1.31 mmol), 2-chloro-6-methylaniline(195 mg, 1.38 mmol), NaO$^t$Bu (152 mg, 1.58 mmol), Pd(dba)$_2$ (15 mg, 0.03 mmol), ligand A (18 mg, 0.05 mmol) in toluene (4 mL) at 105° C. for 2 hours. The experimental procedure described for the synthesis of compound 2a-1 was generally followed. $^1$H NMR (CDCl$_3$): δ 7.51 (m, 2H, ArH), 7.36 (d, 1H, J=7.9 Hz, ArH), 7.19 (d, 1H, J=7.3 Hz, ArH), 7.13–7.06 (m, 2H, ArH), 6.83 (t, 1H, J=7.3 Hz, ArH), 6.27 (d, 1H, J=7.9 Hz, ArH), 4.17 (m, 2H, O—CH—CH—O), 3.97 (m, 2H, O-CH—CH-O), 2.23 (s, 3H, Me), 1.89 (s, 3H, Me). $^{13}$CNMR (CDCl$_3$): δ 142.4, 137.4, 136.8, 131.2, 129.3, 128.8, 127.5, 126.8, 126.4, 125.3, 118.5, 113.5, 109.6, 64.1, 24.1, 18.8. Anal. for C$_{17}$H$_{18}$ClNO$_2$; Calcd: C, 67.21; H, 5.97; N, 4.61; Found: C, 66.92; H, 5.83; N, 4.53.

Example 4: 2-[2'(2-Isopropylanilinophenyl)]-1,3-dioxolane (2b-3): Compound 2b-3 (354 mg, 90% yield) was obtained as a yellow oil from the reaction of 2-(2'-bromophenyl)-1,3-dioxolane (321 mg, 1.40 mmol), 2-isopropylaniline (199 mg, 1.47 mmol), NaO$^t$Bu (141 mg, 1.47 mmol), Pd(dba)$_2$ (16 mg, 0.03 mmol), ligand A (27 mg, 0.08 mmol) in toluene (4 mL) at 105° C. for 75 minutes. The experimental procedure described for the synthesis of compound 2a-1 was generally followed. $^1$H NMR (CDCl$_3$): δ 7.45 (d, 1H, J=7.6 Hz, ArH), 7.33–7.12 (m, 4H, ArH), 7.05 (t, 1H, J=7.4 Hz, ArH), 6.85 (t, 1H, J=7.4 Hz, ArH), 6.68 (br.s, 1H, NH), 5.93 (s, 1H, O—CH—O), 4.10 (m, 4H, O—CH$_2$—CH$_2$—O), 3.13 (septet, 1H, J=6.8 Hz, CHMe$_2$), 1.26 (d, 6H, J=6.8 Hz, 2 Me's). $^{13}$C NMR (CDCl$_3$): δ 143.8, 140.0, 139.5, 129.7, 127.2, 126.3, 126.1, 123.7, 122.9, 121.6, 118.9, 115.5, 103.0, 64.9, 27.8, 22.8. Anal. for C$_{18}$H$_{21}$NO$_2$; Calcd: C, 76.29; H, 7.47; N, 4.94; Found: C, 75.75; H, 7.96; N, 4.81.

Example 5: 2-[(2',4',6'-trimethylphenyl)amino]benzaldehyde (3a-1). In an oven-dried 500 mL Schlenk flask were added sodium t-butoxide (5.77 g, 60.0 mmol, Aldrich), Pd(dba)$_2$ ( 0.144 g, 0.250 mmol, ACROS), ligand A (0.174 g, 0.500 mmol) and 1a (14.45 g, 62.6 mmol). Toluene (130 mL, anhydrous, Aldrich) and 2,4,6-triethylaniline (8.71 g, 64.4 mmol, Aldrich) were added and the reaction was heated to 105 C. for 6 hrs. An additional 1.44 g of sodium t-butoxide was added to the reaction and the reaction was heated at the same temperature for an additional 1 hr, at which time a GLC analysis revealed the reaction was completed. The reaction was cooled to room temperature. The reaction mixture was diluted with 100 mL of ether and washed with 200 mL each of water and sat. aqueous NaCl, dried over anhydrous sodium sulfate, filtered and concentrated in vacuo, affording 20.1 g of a red oil as crude product. The crude material was chromatograghed through a 6×15 cm silica gel column (1–5 % step gradient of ether in hexanes). During this operation, the acetal was partially hydrolyzed. The fractions containing the acetal and the aldehyde were combined and concetrated in vacuo, affording 16.61 g of a yellow viscous oil. The oil was stirred in a mixture of THF (50 mL), water (25 mL), and acetic acid (25 mL) at 22° C. for I hr. THF was removed by evaporation and 200 mL of ether was added. The organic phase was washed with 100 mL each of water and sat. aqueous sodium bicarbonate, dried over anhydrous sodium sulfate, filtered and concentrated in vacuo, affording 14.47 g of a deep yellow viscous oil (97%). A GLC analysis and H-NMR analysis indicated this material was pure. $^1$H NMR (CDCl$_3$, 300 MHz): 9.97 (s, 1H), 9.50 (s, 1H), 7.56 (d, J=7.8 Hz, 1H), 7.3–7.2 (m, 4H), 6.98 (s, 2H), 6.74 (t, J=7.5 Hz, 1H), 6.24 (d, J=8.4 Hz, 1H), 2.34 (s, 3H), 2.16 (s, 6H) ppm. $^{13}$C NMR (CDCl$_3$, 75 MHz): 194.3, 149.9, 136.5, 136.4, 136.3, 135.7, 133.6, 129.2, 118.3, 115.7, 112.3, 20.9, 18.1 ppm.

Example 6: 2-[2',6'-(diisopropylphenyl)amino] benzaldehyde (3a-2). In an oven-dryed 250 mL Schlenk flask were added sodium t-butoxide (2.88 g, 30.0 mmol, Aldrich), Pd(dba)$_2$ (72 mg, 0.13 mmol, ACROS), ligand A (87 mg, 0.25 mmol). Toluene (100 mL, anhydrous, Aldrich), 1 (5.70 g, 24.6 mmol), and 2,6-diisopropylaniline (4.37 g, 24.6 mmol, Aldrich) were added and the reaction was heated to 105 C. for 14 hrs, at which time a GLC analysis revealed the reaction was completed. The reaction was cooled to room temperature. The reaction mixture was stirred with 50 mL of water and filtered to remove insoluble materials. The organic layer was separated and washed with 50 mL of sat. aqueous NaCl, dried over anhydrous sodium sulfate, filtered and concentrated in vacuo, affording 8.88 g of a red oil as crude product. The crude material was subjected to hydrolysis in the similar way as 3a-1 ( THF (50 mL), water (25 mL), and acetic acid (25 mL) at 22 C. for 1 hr). The crude product was purified by flash chromatography on a 7×20 cm silica gel column (2.5% ether in hexanes), affording 6.68 g of a very yellow viscous oil (96 %). IR (liquid film) 3292, 1660 cm$^{-1}$. $^1$H—NMR (300 MHz, CDCl$_3$) δ 1.08 (d, 3H, J=6.9 Hz), 1.13 (d, 3H, J=6.9 Hz), 3.04 (sept, 2H, J=6.9 Hz), 6.20 (d, 1H, J=8.5), 6.70 (t, 1H, J=7.4 Hz), 7.18–7.23 (m, 3H), 7.32 (t, 1H, J=7.6 Hz), 7.53 (dd, 1H, J=7.8, 1.5 Hz), 9.54 (br.s, 1H), 9.94 (s, 1H). $^{13}$C—NMR (75 MHz, CDCl$_3$) δ 23.0, 24.5, 28.4, 112.5, 115.7, 118.0, 123.9, 128.0, 133.4, 135.5, 136.1, 147.3, 151.0, 194.2. Mass spectrum (EI+) m/e 281 (M+), 266 (bp).

Example 7: This example is a general procedure for the formation of 2-mesitylaminobenzaldehyde imines: To a solution of 2-mesitylaminobenzaldehyde 3a-1 (957 mg, 4 mmol) in dichloroethane (6 mL) was added benzylamine (429 mg, 4 mmol) via syringe, followed by a catalytic amount of p-toluenesulfonic acid monohydrate (18 mg, ~1%) and 4Å molecular sieves. The reaction was heated to reflux overnight while stirring under argon. The disappearance of the aldehyde and formation of the imine was followed by GC/MS. To the crude product was added amino propyl silica and the mixture was shaken. The mixture was then filtered and the resulting solution was concentrated. The product was then precipitated with hexanes. The precipitate was washed with cold hexanes and dried in vacuo. 4a-1: $^1$H NMR (CDCl$_3$, 300 MHz): 10.49 (s, 1H), 8.57 (s, 1H), 7.4–7.25 (m, 6H), 7.12 (t, J=8 Hz, 1H) 7.01 (s, 1H), 6.69 (t, J=8 Hz, 1H), 6.26 (d, J=8 Hz, 1H), 4.69 (s, 2H), 2.32 (s, 3H), 2.13 (s, 6H) ppm. $^{13}$C NMR (CDCl$_3$, 75 MHz): 165.3, 148.3, 139.8, 136.3, 135.5, 135.2, 133.8, 131.2, 128.9, 128.4, 127.6, 126.8, 116.9, 115.1, 111.5, 65.12, 20.9, 18.2 ppm. GC-MS: m/z 328 (M)$^+$. 4a-2: $^1$H NMR (CDCl$_3$, 300 MHz): 10.7 (s, 1H), 8.74 (s, 1H), 7.48 (d, J=8 Hz, 1H), 7.33 (d, J=8 Hz, 1H), 7.2 (m, 4H), 7.05 (s, 2H), 6.79 (t, J=8 Hz, 1H), 6.35 (d, J=8 Hz, 1H), 3.01 (m, 6.9 Hz, 1H), 2.40 (s, 3H), 2.28 (s, 6H), 1.34 (d, J=6.9 Hz, 6H) ppm. $^{13}$C NMR (CDCl$_3$, 75 MHz): 162.3, 148.5, 146.5, 136.3, 135.7, 135.1, 134.5, 131.9, 129.0, 127.1, 120.9, 117.3, 115.4, 111.8, 33.7, 24.1, 20.9, 18.3 ppm. GC-MS: m/z 356 (M)$^+$.

Example 8: This example is a general procedure for the formation of 2-(2,6-diisopropylphenyl)aminobenzaldehyde imines. To a solution of 2-[(2,6-diisopropylphenyl) amino] benzaldehyde 3a-2 (126 mg, 0.45 mmol) in dichloroethane (500 μL) was added 2,6-diisopropylaniline (84 μL, 0.45 mmol) via syringe, followed by a catalytic amount ofp-toluenesulfonic acid monohydrate (10 mg, 10%). The resulting solution was concentrated and the resulting oil was heated overnight (external temperature 120 ° C.). The disappearance of the aldehyde and formation of the imine was followed by GC/MS. To the crude product was added dichloroethane (1 mL) followed by amino propyl silica and the mixture was shaken. The mixture was then filtered and the resulting solution was concentrated. The product was then precipitated with methanol. The precipitate was washed with cold methanol and dried in vacuo. 4a-3: $^1$H NMR (CDCl$_3$, 300 MHz): 10.56 (s, 1H), 8.40 (s, 1H), 7.4–7.1 (m, 8H), 6.74 (t, J=7 Hz, 1H), 6.34 (d, J=8 Hz, 1H), 3.25 (m, 2H), 3.14 (m, 2H), 1.3–1.1 (m, 24H) ppm. $^{13}$C NMR (CDCl$_3$, 75 MHz): 166.2, 150.4, 147.9, 138.6, 134.9, 134.8, 132.6, 127.9, 124.8, 124.2, 123.5, 116.6, 115.5, 112.4 ppm. GC-MS: m/z440 (M)$^+$.

Example 9: This example is a general procedure for the formation of 2-mesitylaminobenzaldehyde 2-aminomethylenes. To 4a-2 (0.17 mmol, 60 mg) in dichloroethane (2 mL) was added acetic acid (60 μL) followed by NaBH(OAc)$_3$ (0.34 mmol, 70 mg). The resulting mixture was shaken at room temperature for 2 hours. The crude product was extracted from an aqueous Na$_2$CO$_3$ solution with dichloroethane (3×2 mL) then passed through a plug of silica gel and concentrated to afford a pale yellow oil. 5a-1: $^1$H NMR (CDCl$_3$, 300 MHz): 7.27 (d, J=7.4 Hz, 1H), 7.3–7.1 (m, 3H), 6.97 (s, 2H), 6.9–6.7 (m, 3H), 6.61 (s, 2H), 6.29 (d, J=8 Hz, 1H), 4.42 (s, 2H), 2.91 (m, J=6.9 Hz, 1H), 2.36 (s, 3H), 2.19 (s, 6H), 1.30 (d, J=6.9 Hz, 6H) ppm. $^{13}$C NMR (CDCl$_3$, 75 MHz): 146.0, 145.8, 139.5, 135.8, 134.7, 134.6, 130.0, 129.1, 128.9, 127.2, 122.8, 117.4, 114.2, 112.2, 48.2, 33.2, 24.2, 20.6, 18.2 ppm. GC-MS: m/z 358 (M)$^+$ It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A complex characterized by one of the following general formulas:

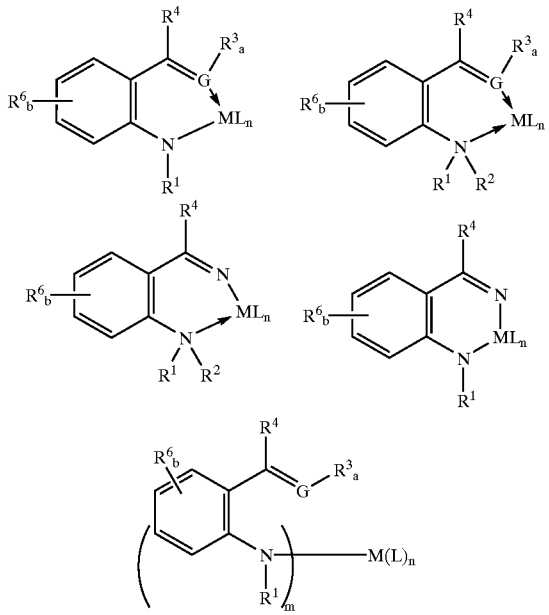

wherein each $R^1$, $R^2$, $R^3$, $R^4$ $R^5$ and $R^6$ is independently selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof; optionally, $R^1$ and $R^2$ are joined together in a ring structure and/or $R^4$ and $R^5$ are joined together in a ring structure;

G is either nitrogen or oxygen and a is 0 or 1 depending on G;

b is 0, 1, 2, 3 or 4;

M is a transition metal selected from the group consisting of Groups 3, 4, 5, 6, 7, 8, 9 and 10 of the Periodic Table of Elements;

L is independently each occurrence, a ligand;

n is a number 0, 1, 2, 3, 4, and 5; and m is 1, 2, 3 or 4.

2. The complex of claim 1, wherein M is selected from the group consisting of Sc, Y, Zr, Ti, Hf, V, Nb, Ta, Cr, Mo, Mn, Fe, Ru, Co, Rh, Ni, Pd, Pt.

3. The complex of claim 2, wherein M is selected from the group consisting of Pd, Ni, Co, Fe, Ru, Rh, Ir, Pt, Cr, Mo, Mn, and V.

4. The complex of claim 1, wherein L is selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof.

5. The complex of claim 1, wherein L is selected from the group consisting of alkene, diene, carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino.

6. The complex of claim 1, wherein $R^1$ is a substituted or unsubstitued phenyl.

7. The complex of claim 6, wherein $R^1$ is a substituted phenyl and there are from 1–5 substituents on said phenyl ring, with each of said substituents independently selected from the group consisting of halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof.

8. The complex of claim 7, wherein there are 1, 2 or 3 substituents on said substituted phenyl and said substituents are selected from the group consisting of chloro, fluoro, iodo, bromo, methyl, ethyl, propyl, butyl, cyclopentyl, cylcohexyl, cyclooctyl, phenyl, naphthyl, benzyl, trimethylsilyl and isomers thereof.

9. The complex of claim 1, wherein $R^4$ is selected from the group consisting of hydrogen, alkyl, substituted alkyl, cycloalkyl, substituted cycloalkyl, heteroalkyl, aryl, substitute aryl, heteroaryl, substituted heteroaryl, alkoxy, aryloxy, amino and silyl.

10. The complex of claim 9, wherein $R^4$ is selected from the group consisting of hydrogen, alkyl, aryl and cycloalkyl.

11. The complex of claim 1, wherein $R^4$ is joined in a ring structure with G and $R^3$, wherein said ring has at least four atoms in the backbone of the ring.

12. The complex of claim 11, wherein G is nitrogen and $R^3$ forms a methylene bridge to $R^4$.

13. The complex of claim 1, wherein G is nitrogen and a is 1 and $R^3$ is selected from the group consisting of hydrogen, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno and combinations thereof.

14. The complex of claim 1, wherein $R^3$ is benzyl or a substituted or unsubstituted phenyl.

15. The complex of claim 14, wherein $R^3$ is a substituted phenyl and there are from 1–5 substituents on said phenyl ring, with each of said substituents independently selected from the group consisting of halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof.

16. The complex of claim 15, wherein there are 1, 2 or 3 substituents on said substituted phenyl and said substituents are selected from the group consisting of chloro, fluoro, iodo, bromo, methyl, ethyl, propyl, butyl, cyclopentyl, cylcohexyl, cyclooctyl, phenyl, naphthyl, benzyl, trimethylsilyl and isomers thereof.

17. The complex of claim 1, wherein $R^6$ is selected from the group consisting of alkyl, aryl and cycloalkyl and b is 1, 2, 3 or 4.

18. The complex of claim 1, wherein b is 2 and the two $R^6$ groups are joined into a substituted or unsubstituted fused ring structure with the benzene ring in the backbone of the compound.

19. The complex of claim 1, wherein G is oxygen and a is 0.

20. The complex of claim 1, wherein each of $R^1$ and $R^2$ is independently selected from the group consisting of alkyl, substituted alkyl, cycloalkyl, substituted cycloalkyl, aryl and substituted aryl.

21. The complex of claim 1, wherein $R^1$ and $R^2$ are joined in a ring, wherein the said ring has between 5 and 10 non-hydrogen atoms.

22. The complex of claim 21, wherein said ring has between 5 and 6 non-hydrogen atoms in the backbone of the ring.

23. The complex of claim 1, wherein each of $R^1$ and $R^2$ is independently selected from the group consisting of hydrogen, alkyl, substituted alkyl, cycloalkyl, substituted cycloalkyl, heteroalkyl, aryl, substitute aryl, heteroaryl, substituted heteroaryl, alkoxy, aryloxy, amino and silyl.

24. The complex of claim 23, wherein each $R^1$ and $R^2$ is independently selected from the group consisting of hydrogen alkyl, aryl and cycloalkyl.

25. A composition of matter comprising the compound of claim 1 and a metal precursor characterized by the general formula $M(L)_n$, where M is a transition metal selected from the group consisting of Groups 3, 4, 5, 6, 7, 8, 9 and 10 of the Periodic Table of Elements; L is independently each occurrence, a ligand; and n is a number 0, 1, 2, 3, 4, and 5.

26. The composition of claim 25 wherein the ratio of compound to metal precursor is in the range of about 0.01:1 to about 100:1.

27. The composition of claim 26 wherein the ratio of compound to metal precursor is in the range of about 0.5:1 to about 20:1.

\* \* \* \* \*

UNITED STATES PATENT AND TRADEMARK OFFICE
CERTIFICATE OF CORRECTION

PATENT NO. : 6,974,878 B2
DATED : December 13, 2005
INVENTOR(S) : Guram et al.

It is certified that error appears in the above-identified patent and that said Letters Patent is hereby corrected as shown below:

Title page,
Item [56], References Cited, OTHER PUBLICATIONS,
"OSA, T et al…" reference, replace "881-7.*" with -- 1881-1887.* --.

Column 24,
Line 4, replace "unsubstitued" with -- unsubstituted --.

Signed and Sealed this

Fourteenth Day of February, 2006

JON W. DUDAS
*Director of the United States Patent and Trademark Office*